United States Patent
Feiweier et al.

(10) Patent No.: US 9,971,007 B2
(45) Date of Patent: May 15, 2018

(54) METHOD AND APPARATUS FOR ACCELERATED MAGNETIC RESONANCE IMAGING

(71) Applicant: Siemens Aktiengesellschaft, Munich (DE)

(72) Inventors: Thorsten Feiweier, Poxdorf (DE); Marcel Dominik Nickel, Herzogenaurach (DE)

(73) Assignee: Siemens Aktiengesellschaft, Munich (DE)

( * ) Notice: Subject to any disclaimer, the term of this patent is extended or adjusted under 35 U.S.C. 154(b) by 465 days.

(21) Appl. No.: 14/823,165

(22) Filed: Aug. 11, 2015

(65) Prior Publication Data
US 2016/0041247 A1 Feb. 11, 2016

(30) Foreign Application Priority Data
Aug. 11, 2014 (DE) .................. 10 2014 215 899

(51) Int. Cl.
| | | |
|---|---|---|
| *G01V 3/00* | (2006.01) | |
| *G01R 33/561* | (2006.01) | |
| *A61B 5/055* | (2006.01) | |
| *G01R 33/56* | (2006.01) | |
| *G01R 33/48* | (2006.01) | |
| *G01R 33/50* | (2006.01) | |
| *G01R 33/485* | (2006.01) | |

(52) U.S. Cl.
CPC ............ *G01R 33/561* (2013.01); *A61B 5/055* (2013.01); *G01R 33/5602* (2013.01); *G01R 33/485* (2013.01); *G01R 33/4818* (2013.01); *G01R 33/4828* (2013.01); *G01R 33/50* (2013.01); *G01R 33/5611* (2013.01); *G01R 33/5616* (2013.01)

(58) Field of Classification Search
USPC ........................................................ 324/309
See application file for complete search history.

(56) References Cited

U.S. PATENT DOCUMENTS

| | | | | |
|---|---|---|---|---|
| 6,448,770 B1 * | 9/2002 | Liu | ..................... | G01R 33/3621 324/307 |
| 2013/0088228 A1 * | 4/2013 | Feiweier | ............ | G01R 33/4838 324/309 |

(Continued)

OTHER PUBLICATIONS

Mekle et al; "Combined MR Data Acquisition of Multicontrast Images Using Variable Acquisition Parameters and K-Space Data Sharing"; IEEE Trans. Med. Imaging; vol. 22; No. 7; pp. 806-823; (2003).
Sodickson, et al: "Simultaneous Acquisition of Spatial Harmonics (SMASH) Fast Imaging with Radiofrequency Coil Arrays", in: Magnetic Resonance in Medicine, vol. 38, pp. 591-603, (1997).

(Continued)

*Primary Examiner* — Rodney Fuller
(74) *Attorney, Agent, or Firm* — Schiff Hardin LLP

(57) ABSTRACT

In a method and apparatus for magnetic resonance (MR) imaging, a result image is provided based on multiple MR contrasts. The result image is indicative of a value of a magnetic parameter. MR data are acquired for the multiple contrasts at different time points, in each case following preparation of a magnetization. During the acquisition of the MR data, k-space is undersampled according to a respective undersampling scheme. The undersampling schemes of the different MR contrasts are different from one another.

17 Claims, 6 Drawing Sheets

(56) References Cited

U.S. PATENT DOCUMENTS

| | | | |
|---|---|---|---|
| 2013/0342206 A1* | 12/2013 | Ugurbil | G01R 33/4835 |
| | | | 324/309 |
| 2014/0091793 A1 | 4/2014 | Guo et al. | |
| 2014/0300352 A1* | 10/2014 | Li | G01R 33/5608 |
| | | | 324/309 |
| 2015/0061667 A1 | 3/2015 | Nickel | |
| 2015/0061672 A1 | 3/2015 | Kannengiesser et al. | |
| 2015/0192653 A1* | 7/2015 | Sharif | A61B 5/055 |
| | | | 600/420 |
| 2015/0287222 A1* | 10/2015 | Zhao | G01R 33/50 |
| | | | 382/131 |
| 2015/0346303 A1* | 12/2015 | Hu | G01R 33/5601 |
| | | | 600/420 |

OTHER PUBLICATIONS

Samsonov,: "A Novel Reconstruction Approach Using Model Consistency Condition for Accelerated Quantitative MRI (MOCCA)", in: Proc. Intl. Soc. Magn. Reson. Med, vol. 20, p. 358; (2012).

Griswold et.al.: "Generalized Autocalibrating Partially Parallel Acquisitions (GRAPPA)", Magnetic Resonance in Medicine, vol. 47, pp. 1202-1210, (2002).

Pruessmann, et al.: "SENSE: Sensitivity encoding for Fast MRI", in: Magn. Reson. Med., vol. 42, pp. 952-962, (1999).

Breuer et al. "Controlled Aliasing in Volumetric Parallel Imaging (2D CAIPIRINHA)", Magnetic Resonance in Medicine, vol. 55, pp. 549-556, (2006).

Blaimer et al.: "Smash, Sense, Pils, Grappa", in: Top. Magn. Reson. Imaging, vol. 15, No. 4, pp. 223-236; (2004).

* cited by examiner

FIG 7
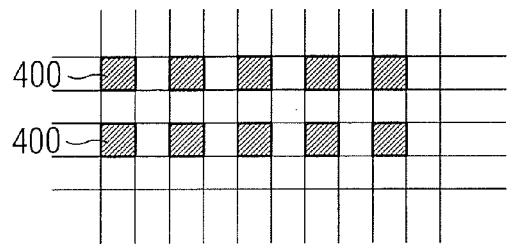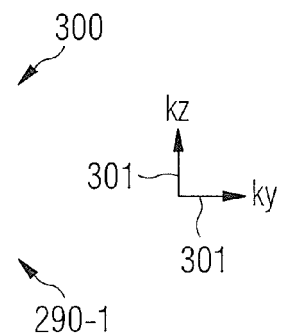
FIG 8
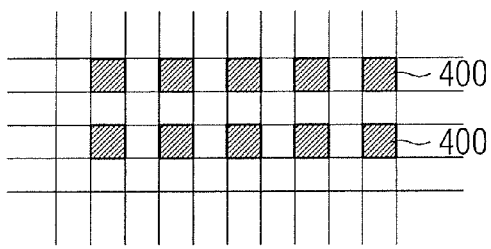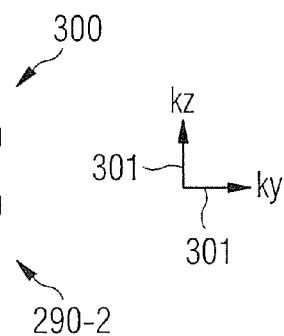
FIG 9
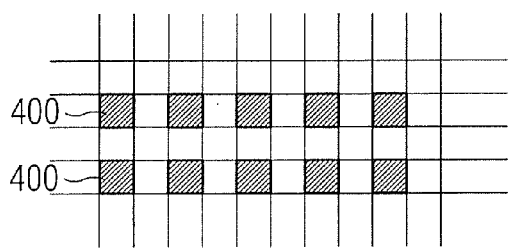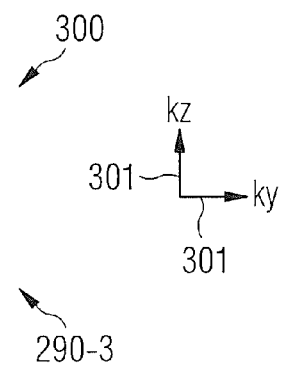
FIG 10
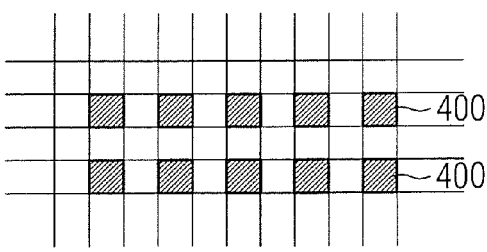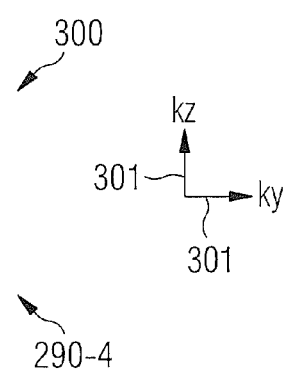

METHOD AND APPARATUS FOR ACCELERATED MAGNETIC RESONANCE IMAGING

BACKGROUND OF THE INVENTION

Field of the Invention

The invention relates to methods for magnetic resonance imaging and to corresponding magnetic resonance systems. The invention relates in particular to magnetic resonance imaging techniques in which different undersampling schemes are used for different magnetic resonance contrasts.

Description of the Prior Art

Magnetic resonance (MR) imaging techniques are known in which a result image is obtained which is indicative of a magnetic parameter in an examination region of interest. For example, the magnetic parameter can correspond to a fraction of a fat spin species or a water spin species in the examination region; in such a case reference is often made to Dixon-type techniques, which allow a water-fat separation. Generally, such techniques which permit the separation of different spin species are also referred to as chemical-shift imaging. It is also possible for the magnetic parameter to correspond e.g. to a T1 relaxation time; in such a case this is often referred to as parametric imaging.

Said aforementioned techniques are frequently based on the acquisition of a number of MR contrasts. The MR contrasts are characterized by the corresponding MR data being acquired at different time points in relation to a magnetic preparation of the magnetization. By adapting a signal model to corresponding MR data of the different MR contrasts it is then possible to determine the respective magnetic parameter.

Parallel imaging techniques (also: parallel acquisition techniques (PAT)) are known for the purpose of accelerating a period of time that is required for performing a corresponding measurement sequence (measurement duration). Typically, PAT techniques are based on an undersampling of k-space; this means that no MR data is acquired for certain k-space points; the missing information is reconstructed subsequently. The so-called acceleration factor quantifies the proportion of those k-space points along a k-space trajectory for which no MR data is acquired. Larger (smaller) acceleration factors typically correspond to a longer (shorter) measurement duration. Typically, a prior known or calibrated sensitivity profile of coils of the RF system is resorted to in order to reconstruct the missing information; this enables aliasing artifacts resulting due to the undersampling to be eliminated or reduced. Typical PAT techniques are e.g.: Generalized Auto-Calibrating Partial Parallel Acquisition (GRAPPA), see e.g. M. A. Griswold et al., in Magn. Reson. Med. 47 (2002) 1202-1210; and Sensitivity Encoding (SENSE), see e.g. K. P. Pruessmann in Magn. Reson. Med. 42 (1999) 952-962; and Simultaneous Acquisition of Spatial Harmonics (SMASH), see e.g. D. K. Sodickson and W. J. Manning in Magn. Reson. Med. 38 (1997) 591-603; and Controlled Aliasing in Volumetric Parallel Imaging (CAIPIRINHA), see e.g. F. A. Breuer et al., Magn. Reson. Med. 55 (2006) 549-556.

It is also known to apply PAT techniques in connection with the Dixon technique or parametric MR imaging. The post-processing in order to determine the result image then happens typically sequentially and separately for different picture elements (pixels) of the different contrasts; in the process, missing MR data can be reconstructed (reconstructed data) first and then the magnetic parameter can be determined by adapting the signal model to the MR data of the different contrasts.

However, such techniques have various limitations and disadvantages. The choice of larger acceleration factors of the PAT technique is often limited by the performance capability of the coil configuration of the respective MR system: a so-called g-factor can increase if a larger acceleration factor is chosen, cf. Eq. 5 from M. Blaimer et al. "SMASH, SENSE, PILS, GRAPPA: How to Choose the Optimal Method" in Top. Magn. Reson. Imaging 15 (2004) 223. The g-factor quantifies a reduction in the signal-to-noise ratio of the reconstructed data as a result of the PAT reconstruction. For this reason it is possible—e.g. given a certain reduction in the measurement duration—to obtain only a comparatively poor signal-to-noise ratio of the MR contrasts; as a result an accuracy with which the MR parameter can be determined may be limited.

SUMMARY OF THE INVENTION

In view of the above, there exists a need for techniques which remove at least some or all of the above-described disadvantages and limitations. There exists a need for improved techniques which enable PAT techniques to be employed within the framework of chemical-shift MR imaging. There also exists a need for improved techniques which enable PAT techniques to be employed within the framework of parametric MR imaging.

An object of the invention is to provide a magnetic resonance imaging method and apparatus that respond to these needs.

In a method for MR imaging according to the invention, a result image of an examination region is acquired based on multiple MR contrasts. MR data are acquired for the multiple MR contrasts at different time points, in each case following preparation of a magnetization of nuclear spins of the subject. The method includes performing a measurement sequence wherein the preparation of the magnetization takes place in the examination region. The performance of the measurement sequence additionally includes, for each MR contrast, the acquisition of MR data for k-space points, wherein during the acquisition of the MR data k-space is undersampled in accordance with a respective undersampling scheme. The undersampling schemes of the different MR contrasts are different from one another. The method furthermore includes determining the result image based on the acquired MR data. Pixel values of pixels of the result image are indicative of a value of a magnetic parameter in the examination region.

The measurement sequence can be a two-dimensional (2D) measurement sequence, for example. However, it is possible for the measurement sequence to be a three-dimensional (3D) measurement sequence. In the latter case the performance of the measurement sequence can be implemented for example, by applying phase encoding steps along a first phase encoding direction and applying phase encoding steps along a second phase encoding direction.

The MR contrasts can therefore designate in each case a set of MR data in the k-space or in the image space which maps the examination region at a specific spatial resolution. The MR contrasts comprise MR data for specific k-space points. MR contrasts adjacent in time can designate such MR contrasts whose assigned time points, following the preparation of the magnetization have—in comparison with other MR contrasts—a minimized temporal spacing.

The result image can be determined based on a signal model. The signal model can link an evolution of the MR data over time—which is mapped by the different MR contrasts—to the magnetic parameter.

Techniques according to the aspect currently under discussion can be applied both in conjunction with chemical-shift MR imaging and in conjunction with parametric MR imaging.

For example, it is possible for the preparation of the magnetization to include the application of a radiofrequency (RF) inversion pulse. This can be desirable in particular in conjunction with parametric MR imaging. The magnetic parameter can then be selected from the following group: T1 relaxation time; T2 relaxation time; saturation magnetization; and flip angle.

However, it would also be possible for the preparation of the magnetization to include the application of an RF excitation pulse. This can be desirable in particular in conjunction with chemical-shift MR imaging. The magnetic parameter can then designate a fraction of a spin species, such as e.g. fat or water, in the examination region.

Generally, it is also possible to apply more than one RF inversion pulse or RF excitation pulse. In connection with parametric MR imaging, for example, a greater number of RF excitation pulses could be applied together with the RF inversion pulse, e.g. in order to determine the T2 relaxation time. In relation to chemical-shift MR imaging, for example, it would be possible to apply multiple RF excitation pulses sequentially for different repetitions; for example, MR data could be acquired in only one part of k-space after each RF excitation pulse; it would then be possible to obtain the MR data of the different MR contrasts by repeating the magnetic preparation and the acquisition of MR data.

The measurement duration can be reduced as a result of the undersampling acquisition of the MR data in accordance with the different undersampling schemes. At the same time, a comparatively large signal-to-noise ratio can be achieved for the different MR contrasts or the result image as a result of using the different undersampling schemes. A noise component caused by the reconstruction by means of PAT techniques can be comparatively small. Accordingly, the magnetic parameter can then be determined with greater precision.

Two undersampling schemes may be different from one another if MR data is acquired at least in part for different k-space points. This can be achieved by means of different k-space trajectories; it is also possible to use identical k-space trajectories, in which case different k-space points along the k-space trajectory are sampled or omitted. It can therefore be possible in general for certain parameters of the different undersampling schemes to be identical, specifically e.g. the respective acceleration factor along different k-space directions and/or the underlying k-space trajectory. The k-space trajectory can designate an ordered sequence of k-space points. MR data can then be acquired for the respective k-space points along the k-space trajectory. Depending on undersampling scheme, the acquisition of MR data for a specific k-space point along the k-space trajectory can be omitted due to the acceleration.

Generally, the undersampling schemes along one k-space direction or along two k-space directions can have an acceleration factor of greater than one. For example, the undersampling schemes along a phase encoding direction ky of the k-space can have an acceleration factor of greater than one. In the case of a 3D measurement sequence, for example, the undersampling schemes can have an acceleration factor of greater than one along the first phase encoding direction of the k-space, and an acceleration factor of greater than one along the second phase encoding direction of the k-space.

Generally, the undersampling schemes can be chosen such that a deviation between the different undersampling schemes has no, or only a minor, systematic characteristic. It would, however, also be possible to choose the undersampling schemes as systematically different. In such a way a systematic sampling of the k-space—considered across all undersampling schemes—can be achieved; this can in turn reduce the noise component caused by the PAT techniques.

For example, the undersampling schemes of the different MR contrasts can have the same acceleration factor along the same k-space directions. Preferably the acceleration factor can be e.g. greater than four, particularly preferably greater than seven.

In particular it is possible, by means of the techniques described in the foregoing, to achieve such a small signal-to-noise ratio for the different MR contrasts that a comparatively large acceleration factor can be chosen. By choosing the acceleration factor to be e.g. greater than four, or particularly preferably greater than seven, a comparatively substantial reduction in the measurement duration can be achieved.

For example, the undersampling schemes of the different MR contrasts can be shifted relative to one another in such a way that MR data is acquired for at least one MR contrast for each k-space point along a predefined k-space trajectory.

This can therefore mean that there is no k-space point along the k-space trajectory for which no MR data is acquired. It may be e.g. possible for each k-space point to be assigned to at least one MR contrast, for which MR data is then acquired for the respective k-space point. In particular, the different undersampling schemes can therefore be chosen such that an overlaying of the undersampling schemes corresponds to a full sampling of k-space, i.e. has no, or no significant, acceleration factor.

It would be possible, for example, for the undersampling schemes of MR contrasts adjacent in time to be shifted by one k-space point along the k-space trajectory in a k-space direction for which the acceleration factor is greater than one.

Therefore, MR data may be acquired for a first k-space point in accordance with a first undersampling scheme and MR data may be acquired for a second k-space point in accordance with a second undersampling scheme, wherein the first and second undersampling schemes are assigned to MR contrasts adjacent in time and the first and second k-space points are arranged adjacent to one another along the k-space trajectory in the k-space. In this way a systematic variation of the undersampling schemes can be achieved from MR contrast to MR contrast; this enables a particularly high quality of the MR contrasts or, as the case may be, a particularly precise determination of the result image.

Generally, a wide variety of k-space trajectories can be implemented. For example, a spiral-shaped k-space trajectory or a radial k-space trajectory could be used. It is, however, also possible to use a Cartesian k-space trajectory in which the k-space points are arranged at regular intervals along a first k-space direction and along a second k-space direction. For example, the k-space points arranged along the Cartesian k-space trajectory can form a rectangular or square grid. It would be e.g. possible for the first and second k-space directions to be oriented orthogonally to one another. For example, the first and second k-space directions can designate two phase encoding directions.

Various aspects in relation to the undersampling schemes have been described in the foregoing. The undersampling schemes describe for which k-space points MR data is acquired. When the MR data has been acquired, the MR contrasts and the result image can be determined. For example, determining the result image can entail, for each pixel of the result image: reconstructing reconstructed data based on a PAT technique. By this means information lost as a result of the undersampling of the k-space can therefore be reconstructed.

Furthermore, determining the result image can entail, for each pixel of the result image: determining the magnetic parameter as a pixel value by adapting the signal model to the respective MR data and/or to the reconstructed data of the different MR contrasts. The reconstructed data can be obtained based on a PAT technique.

In a simple implementation it is possible, for example, for the different MR contrasts to be determined in the first instance. PAT techniques which provide reconstructed data can be used for that purpose. The PAT techniques can operate in the k-space, as is the case e.g. for GRAPPA or CAIPIRHINA. It is also possible for the PAT techniques to operate at least partially in the image space, as is the case e.g. with SENSE. Insofar as the k-space techniques operate in k-space, the reconstructed data can correspond to the MR data of omitted k-space points along the k-space trajectory. Otherwise, image space data can be reconstructed directly. By this means those MR contrasts can then be obtained which have a comparatively high resolution or map a large examination region and exhibit no, or no significant, aliasing artifacts. The PAT techniques are generally known to the person skilled in the art, so no further details need to be explained here.

In such an implementation it may then be possible to adapt the signal model in each case for each pixel of the result image in a second step to the corresponding MR data or, as the case may be, to the reconstructed data of the MR contrasts. The reconstruction or antialiasing can therefore be carried out initially by means of PAT techniques and then the signal model can be adapted to the data obtained in that way. This can enable a particularly simple or rapid implementation of the determining of the result image.

It is also possible for the reconstruction of the reconstructed data and the determination of the magnetic parameter to take place in an interconnected optimization step.

In other words it may be possible, in a single numeric optimization—which determines e.g. an extreme value of a magnitude for a parameter space as solution—to carry out both the reconstruction by means of PAT techniques and the adaptation of the signal model within the framework of chemical-shift MR imaging or parametric MR imaging. It may then be unnecessary to reconstruct missing information initially in a separate first step and reduce aliasing artifacts. This can enable the determining of the result image to be carried out in a particularly precise and rapid manner.

Particularly in connection with chemical-shift MR imaging it may be possible for the optimization step to include non-linear optimization techniques. For a number of pixels of the result image, the determining of the magnetic parameter may additionally include performing a phase unwrapping operation in order to accomplish a phase correction of the respective pixel. The phase unwrapping, for example, may take into account results of the non-linear optimization of a plurality of pixels of the result image which are adjacent to the respective pixel. Analogous techniques are known to the person skilled in the art e.g. from the patent applications DE 10 2013 217 651.1 and DE 10 2013 217 650.3.

According to a further aspect, the invention relates to an MR system. The MR system is configured to provide a result image of an examination subject based multiple of MR contrasts. MR data are acquired for the multiple MR contrasts at different time points in each case following preparation of a magnetization. The MR system has a transmitter/receiver unit (scanner). The transmitter/receiver unit is configured to perform a measurement sequence and in the course of the performance of the measurement sequence to prepare the magnetization in the examination region. The transmitter/receiver unit is additionally configured to acquire MR data for k-space points for each MR contrast in the course of the performance of the measurement sequence. The transmitter/receiver unit is additionally configured to undersample the k-space in accordance with a respective undersampling scheme for each MR contrast during the acquisition of the MR data. The undersampling schemes of the different MR contrasts are different from one another. The MR system additionally comprises a computing unit which is configured to determine the result image based on the acquired MR data. Pixel values of pixels of the result image are indicative of a value of a magnetic parameter in the examination region.

According to this aspect of the invention, the MR system can, for example, be configured to perform the method for MR imaging according to the aforementioned aspect of the present invention.

Results can be achieved for such an MR system that are comparable to the results that can be achieved for the method for MR imaging according to the present invention.

According to a further aspect, the invention relates to a further version of the method for MR imaging. The method provides a result image of an examination region based on multiple MR contrasts. MR data is acquired for the multiple MR contrasts at different time points in each case following preparation of a magnetization. The method includes performing a measurement sequence. The performance of the measurement sequence includes preparing the magnetization in the examination region. The performance of the measurement sequence additionally includes, for each MR contrast: acquiring MR data for k-space points. During the acquisition of the MR data, k-space is undersampled in accordance with a respective undersampling scheme. The method additionally includes determining the result image. Pixel values of pixels of the result image are indicative of a value of a magnetic parameter in the examination region. The determining of the result image comprises, for each pixel, the reconstruction of reconstructed data based on a PAT technique. The determining of the result image additionally comprises, for each pixel of the result image, determining the magnetic parameter as a pixel value by adapting a signal model to the respective MR data and/or to the reconstructed data of the different MR contrasts. The reconstruction and determination of the magnetic parameter take place in an interconnected optimization step.

As a result of the combined reconstruction and adaptation of the signal model, a particularly simple, rapid and precise determination of the result image can be made possible.

According to a further aspect, the present invention relates to a further MR system for MR imaging. The MR system is configured to provide a result image of an examination region based on multiple MR contrasts. MR data are acquired for the multiple MR contrasts at different time points in each case following preparation of a magnetization. The MR system has a transmitter/receiver unit (scanner). The transmitter/receiver unit is configured to perform a measurement sequence and in the course of the performance of the measurement sequence to prepare the magnetization in the examination region. The transmitter/receiver unit is additionally configured to acquire MR data for k-space points for each MR contrast in the course of the performance of the measurement sequence. The transmitter/receiver unit is additionally configured to undersample k-space in accordance with a respective undersampling scheme for each MR contrast during the acquisition of the MR data. The undersampling schemes of the different MR contrasts are different from one another. The MR system additionally comprises a computing unit. The computing unit is configured to determine the result image. Pixel values of pixels of the result image are indicative of a value of a magnetic parameter in the examination region. The computing unit is additionally configured to reconstruct reconstructed data based on a PAT technique in the course of the determination of the result image. The computing unit is additionally configured to determine the magnetic parameter as a pixel value by adapting a signal model to the respective MR data of the different MR contrasts and/or to the reconstructed data. The computing unit is additionally configured to perform the reconstruction of the MR data and the determination of the magnetic parameter in an interconnected optimization step.

This further version of the MR system can, for example, be configured to perform the further version of the method for MR imaging according the present invention.

Results can be achieved for such a MR system that are comparable to the results that can be achieved with the further version of the method for MR imaging according to the present invention.

BRIEF DESCRIPTION OF THE DRAWINGS

FIG. 7 shows an undersampling scheme for a first MR contrast for the k-space trajectory of FIG. 3, wherein an image acceleration is performed along a first phase encoding direction and a second phase encoding direction.

FIG. 8 shows an undersampling scheme for a second MR contrast which is shifted relative to the undersampling scheme for the first MR contrast according to FIG. 7 along the first phase encoding direction.

FIG. 9 shows an undersampling scheme for a third MR contrast which is shifted relative to the undersampling scheme for the first MR contrast according to FIG. 7 along the second phase encoding direction.

FIG. 10 shows an undersampling scheme for a fourth MR contrast which is shifted relative to the undersampling scheme for the first MR contrast according to FIG. 7 along the first phase encoding direction and along the second phase encoding direction.

DESCRIPTION OF THE PREFERRED EMBODIMENTS

Figure 1:
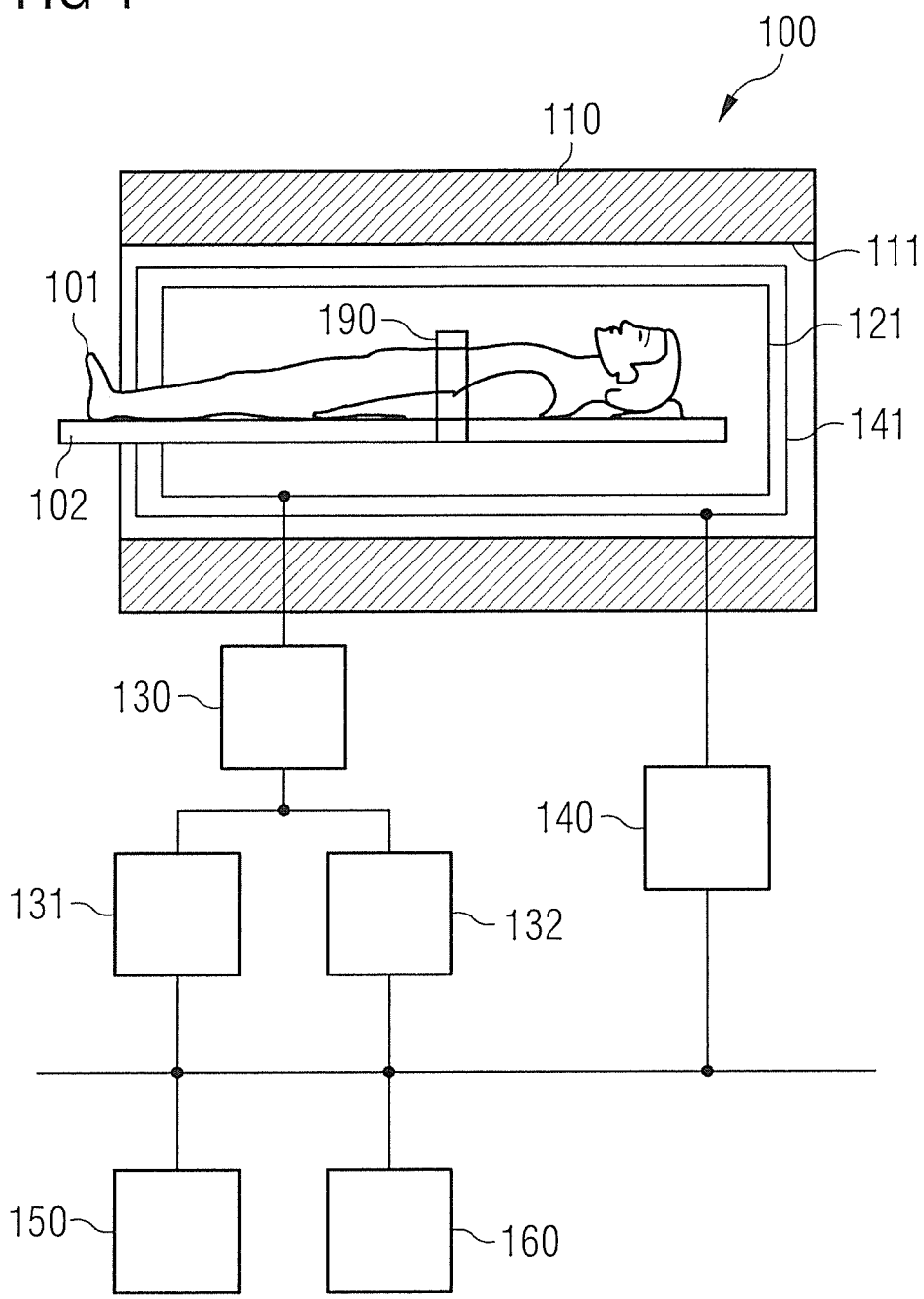
FIG. 1 is a schematic view of an MR system.

The invention is explained in more detail below with reference to the drawings. In the figures, like reference signs designate identical or similar elements. The figures are schematic representations of different embodiment variants of the invention. Elements shown in the figures are not necessarily drawn to scale. Rather, the different elements represented in the figures are depicted in such a way that their function and general purpose are rendered intelligible to the person skilled in the art. Connections and couplings represented in the figures between functional units and elements may also be implemented as an indirect connection or coupling. A connection or coupling may be implemented as wired or wireless. Functional units may be implemented in the form of hardware, software or a combination of hardware and software.

PAT techniques are explained in the following in connection with chemical-shift MR imaging or parametric MR imaging. The shifting of the undersampling scheme used during the acquisition of MR data of different MR contrasts enables the noise amplification to be reduced; in particular it is possible in this way to realize a scenario in which the g-factors of the PAT technique stand in relation to an overlaying of the different undersampling schemes. The overlaying of the different undersampling schemes can correspond to a lower acceleration factor than each individual undersampling scheme. Given suitable choice of the different undersampling schemes, it is therefore possible to achieve a comparatively large signal-to-noise ratio of the reconstructed data.

Furthermore, the techniques described herein—compared to conventional iterative techniques using corresponding undersampling—allow a comparatively lower numeric complexity during the reconstruction and in the adaptation of a signal model. A known aliasing of the acquired MR data is exploited for the different MR contrasts. Instead of pixel-by-pixel post-processing, overlapping pixels are preferably processed in an interconnected optimization step.

Below it is demonstrated with the use of a theoretical consideration to what extent the effect of a reduction in signal noise due to PAT techniques can be achieved when different undersampling schemes are used.

Preliminary Observations on PAT Techniques

Various basic principles in relation to the PAT techniques are explained below. For the sake of simplicity, the following description is limited to SENSE techniques; similar discussions can be easily extended to GRAPPA techniques by performing an image-based GRAPPA reconstruction with adaptive coil combinations, i.e. by means of Fourier transformation of GRAPPA weights into the image space point.

With SENSE, the image $M(x)$ is calculated by minimizing the data consistency term $$\chi^2 = \sum_{l,k \in R\text{-}grid} \left| d_l(k) - \sum_x u_{kx} C_l(x) M(x) \right|^2, \quad (1)$$

where $d_l(k)$ denotes the acquired MR data for the I-th coil, measured on a regular undersampled grid with acceleration factor R. $u_{kx}$ denotes the unitary discrete Fourier transform, and $C_l(x)$ the I-th coil sensitivity at position x. It is furthermore assumed that the data has been decorrelated and noise levels have been normalized.

Fourier-transforming the argument by means of zero-padding for such k-space points for which no MR data has been acquired yields:

$$\chi^2 = R \sum_{y \in reduced\text{-}FOV} \left( \sum_l \left| D_l(y) - \sum_x P_{y-x}^{R,\delta} C_l(x) M(x) \right|^2 \right), \quad (2)$$

where $D_l(y) = \sum_{k \in R\text{-}grid} u^*_{ky} d_l(k)$ is an R-times aliased image and the sum over the index y can therefore be limited to an R-th part of an imaged region.

In the following, the vector $P_{y-x}^{R,\delta} = \sum_{k \in R\text{-}grid} u^*_{ky} u_{kx}$ acquires special significance. This vector is only non-vanishing for R values of y−x. Furthermore, the undersampling scheme is not unique, but can be shifted to R different positions. These positions are indexed by δ. For example, the following can apply:

$$\sum_{\delta=1}^{R} P_{y-x}^{R,\delta} \alpha \delta_{x,y} .. \quad (3)$$

According to various aspects it is then possible to use different undersampling schemes for different MR contrasts in order to improve the noise propagation when the MR contrasts are combined by adapting a signal model to the MR contrasts.

Preliminary Observations on Parametric MR Imaging

For parametric MR imaging, in particular T1 and T2 mapping, the signal of different MR contrasts stands in relation to a signal model. The parameters are extracted by adapting the signal model to the different MR contrasts. Typically, this is achieved by means of fitting techniques. This can, however, also be achieved by comparing with a precalculated model dataset, as is common practice e.g. in what are termed fingerprint techniques. Another technique in this context would be adapting to approximations, e.g. a linearization which is obtained by means of principal component analysis; see in this regard e.g. A. Samsonov "A Novel Reconstruction Approach Using Model Consistency Condition for Accelerated Quantitative MRI (MOCCA)" in Proc. Intl. Soc. Mag. Reson. Med. 20 (2012) 358.

For the specific example of Look-Locker-type inversion recovery, for example, the I-th MR contrast is given as a function of a proton density $\rho(x)$, relaxation time $T_1(x)$ and flip angle $\beta_l(x)$. This is equivalent to an adaptation of the saturation magnetization:

$$M(x,i) = F(\rho(x), T_1(x), \alpha(x), i). \quad (4)$$

Generally, it can be assumed:

$$M(x,i) = F(p(x), i), \quad (5)$$

where $p(x)$ is the vector of the MR parameters.

Combination of PAT Techniques with Parametric MR Imaging

When different undersampling schemes are used for the different MR contrasts, the signal model stands in relation to the acquired MR data according to the following equation:

$$\chi^2 = R \sum_{y \in reduced\text{-}FOV} \left( \sum_i \sum_l \left| D_l(y,i) - \sum_x P_{y-x}^{R,\delta_i} C_l(x) F(p(x), i) \right|^2 \right), \quad (6)$$

where the undersampling schemes are shifted according to $\delta_i$ for the different MR contrasts.

A notation with vector $y_{\{l,i\}} = D_l(y,i)$ is introduced for the aliased coil images, where $l \in 1, \ldots, N_{coils}$ and $i \in 1, \ldots, N_{contrasts}$ applies. In addition, the matrix $A_{\{l,i\},\{x_j\}} = P_{y-x_j}^{R,\delta_i} C_l(x_j)$ is introduced, where the index $j=1, \ldots, R$ runs across the aliased pixels/voxels. Because the minimization decouples for each y in the reduced field of view, a remaining problem consists in minimizing the following term:

$$\tilde{\chi}^2 = \sum_{\{l,i\}} \left| y_{\{l,i\}} - \sum_x A_{\{l,i\},x} F(p(x), i) \right|^2. \quad (7)$$

This can be solved by means of optimization techniques corresponding to those of conventional parametric MR imaging.

Various effects and advantages which can be achieved by shifting the undersampling schemes of the different MR contrasts are explained below. In the event that no shifting is performed, the reconstruction of reconstructed MR data based on the PAT technique and the adaptation of the signal model are decoupled. Higher acceleration factors are limited by the noise amplification due to the PAT technique. Insofar as different undersampling schemes are used for the different MR contrasts, the effective noise amplification corresponds more to an overlaying of the different undersampling schemes and is therefore less serious. A coupled reconstruction of the reconstructed MR data and adaptation of the signal model can also take place.

The advantage can be expressed as noise propagation. As explained hereinabove, it is assumed for simplicity that the MR data have been decorrelated and noise levels in each channel have been normalized. This means that the covariance matrix can be notated as:

$$\langle y_{\{l,i\}} y_{\{J,j\}}^\dagger \rangle = \sigma^2 \delta_{I,J} \delta_{i,j}. \quad (8)$$

Under the assumption that p(x) has been optimized, the linearization yields:

$$\Delta y_{\{l,i\}} = \sum_{x,m,y} A_{\{l,i\},x} \frac{\partial F(p(x), i)}{\partial p_m(y)} \Delta p_m(y) \quad (9)$$
$$\equiv \sum_{x,m,y} A_{\{l,i\},x} J_{\{i,x\},\{y,m\}} \Delta p_m(y)$$
$$\equiv \sum_{x,m} B_{\{l,i\},\{x,m\}} \Delta p_m(x).$$

The noise correlation in the determined parameters is then obtained as:

$$\langle p_m(x) p_n(y)^\dagger \rangle = \sigma^2 (B^\dagger B)^{-1}_{\{m,x\},\{n,y\}}. \quad (10)$$

An example of the effect of the above-described techniques of undersampling schemes that are shifted relative to one another is accessible for the simple case in which no change is obtained for different MR contrasts, i.e.:

$$F(p(x),i)=\rho(x). \quad (11)$$

In this case the following is obtained $$J_{\{i,x\},\{y,m\}}=\delta_{x,y}\delta_{m,0}, \quad (12)$$

and consequently $$B_{\{I,i\},\{x,m\}}=A_{\{I,i\},x}. \quad (13)$$

What is obtained in this case, therefore, is a g-factor of the noise amplification which corresponds to an overlaying of the undersampling schemes. In the case of a large number of MR contrasts, the noise amplification is reduced significantly when undersampling schemes are used which are shifted e.g. systematically from MR contrast to MR contrast—generally up to the point at which the signal noise does not result from the PAT techniques used, but is due solely to the reduced measurement duration.

An explicit example is explained below. The conventional Look-Locker technique for parametric MR imaging in respect of the MR parameter of the $T_1$ relaxation time comprises the application of an RF inversion pulse, followed by continuous flash acquisitions in order to acquire MR data. From said acquisitions, MR contrasts are determined at known time points after the inversion, and are then used to perform a pixel-based fit in respect of magnetization, saturation magnetization and effective $T_1$. The magnetization, the $T_1$ relaxation time $T_1$ and the flip angle map of the flash acquisition can be obtained from said parameters.

For motion-sensitive applications, the acquisition of the MR data within the context of the flash technique is typically performed continuously for a single image, i.e. no segmentation is present in relation to a plurality of RF inversion pulses. Since the target range for the $T_1$ relaxation time $T_1$ typically amounts to approximately 300 ms to 1500 ms, the acquisition of the MR data for a single MR contrast should be performed in less than 200 ms. For a repetition time $T_R$ of approximately 4 ms, this gives approx. 50 phase encoding steps for a single MR contrast.

The combination of PAT techniques and parametric MR imaging can be realized in two ways for these applications: Firstly, the acceleration for the acquisition of MR data for a single MR contrast can be increased to acceleration factors of $\geq 6$, which thereby enables a higher resolution of the parametric MR imaging in the same time. Secondly, it may be possible to increase the acceleration factor for the acquisition of MR data for a single MR contrast to $\geq 6$ and the acquisition of different slices can be accomplished by means of interleaving techniques.

Preliminary Observations on Chemical-Shift MR Imaging

For water-fat separation based on Dixon techniques, MR contrasts for different echo times stand in relation to a signal model which contains water, fat, a number of echoes and different phases/fields and, in appropriate cases, effective relaxation times. Typically, the determination of the MR parameter is achieved by fitting the complex-value signal model or its magnitude to the acquired MR data. The different MR parameters of the signal model can be determined in this way. Typically, more than one minimum value per pixel or voxel is obtained for the phases/fields. A phase unwrapping can then be performed in order to determine the physically relevant minimum in each pixel/voxel. This is based on the knowledge that phases/fields vary only slightly as a function of the location. The signal model at position x for the e-th echo is given by:

$$M_e(x) = (W(x) + c_e F(x))e^{i\phi_e(x) - R_2^*(x)T_1} \quad (14)$$
$$= e^{i\phi_e(x) - R_2^*(x)T_E} \sum_m c_{e,m} V_m(x),$$

where W(x) is the fraction of the water component, F(x) is the fraction of the fat component, V(x)={W(x),F(x)} is a combined vector made up of the water component and the fat component, $c_e$ is the dephasing of the fat component for the e-th echo, and $c_{e,m}$ is its generalization containing the water component. Apart from this, $R_2^*(x)$ is the effective relaxation time and $T_e(x)$ the echo time. In addition, $\varphi_e(x)$ is the phase of the e-th echo. There are various models for $\varphi_e(x)$, including:

$\varphi_e(x)$ can assume different values for different echo times. This can be necessary in particular for a case in which only two echoes are present and W(x) and F(x) are assumed to be real-valued;

$\varphi_e(x)=\omega(x)T_E+\varphi(x)$, where $\overline{\omega}(x)$ is the offset frequency at pixel/voxel x. The phase $\varphi(x)$ is only required if W(x) and F(x) are assumed to be real-valued; and $\varphi_e(x)=\omega(x)T_E+\varphi(x)+\delta_e\varphi_{EC}(x)$, where $\overline{\omega}(x)$ is the offset frequency at pixel/voxel x. The phase $\varphi(x)$ is only required if W(x) and F(x) are assumed to be real-valued; in addition, $\vartheta_c=1$ applies to echoes having a readout gradient in one direction and $\overline{\omega}_c=-1$ to echoes having gradient pulses in the opposite direction.

Generally, more than two chemical components, e.g. additionally silicon, and more than one effective relaxation time, e.g. for each chemical component, can be taken into account in connection with chemical-shift MR imaging. Generally, W(x) and F(x) can be assumed to be real-valued or complex-valued, e.g. as a function of the signal model for the phases.

Combination of PAT Techniques with Chemical-Shift MR Imaging

If undersampling schemes shifted relative to one another are used for each MR contrast, the signal model stands in relation to the acquired MR data by means of the following relation:

$$\chi^2 = R \sum_{y \in reduced-FOV} \left( \sum_e \sum_I \left| D_I(y,e) - \sum_x P_{y-x}^{R,\delta_e} C_I(x) M_e(x) \right|^2 \right), \quad (15)$$

where $D_I(y,e)$ is the aliased image of the I-th coil and of the e-th echo. In addition, the undersampling schemes are shifted relative to one another along the different echoes, as is specified by $\delta_e$.

Below, a notation with the vector $$y_{\{I,e\}} = D_I(y,e) \quad (16)$$

is introduced for the aliased coil images, where $I \in 1, \ldots, N_{coils}$ and $e \in 1, \ldots, N_{echoes}$. In addition, the matrix $$A_{\{I,e\},\{x_j\}} = P_{y-x_j}^{R,\delta_e} C_I(x_j) \quad (17)$$

is introduced with the indices $j=1, \ldots, R$, where the indices designate the aliased pixels/voxels as a sequence number. Since the minimization decouples for each y located in the reduced field of view, the remaining problem consists in minimizing the following expression:

$$\tilde{\chi}^2 = \sum_{\{I,e\}} \left| y_{\{I,e\}} - \sum_{x,m} A_{\{I,e\},x} \phi_e(x) c_{e,m} V_m(x) \right|^2, \quad (18)$$

where $$\varphi_e(x) = t e^{i\varphi_e(x) - R_2^*(x) T_E}. \quad (19)$$

This optimization can be solved in an analogous manner as for a pixel-based post-processing operation. The conventional approach is to eliminate the water component and the fat component by variable projection and then to perform a non-linear optimization for different phase candidates. The correct minimum is ultimately determined by means of a phase unwrapping which assumes constant phase maps, and by selecting the best fitted minimum or a minimum therebetween.

Advantages and effects of the shifting of the undersampling schemes for the different MR contrasts are explained hereinbelow. For the case in which the MR data of the different MR contrasts is acquired each time using the same undersampling scheme, the reconstruction based on PAT techniques and the adaptation of the signal model can be decoupled. If higher acceleration factors are used for the acquisition of the MR data for an individual MR contrast, the choice of the acceleration factor is limited by the noise amplification of the PAT techniques. In the case of the undersampling schemes shifted relative to one another, the effective noise amplification is closer to the case of the overlaying of the undersampling schemes shifted relative to one another. For this reason the effective noise amplification is less strong. Furthermore, the determining of the result image can be accomplished by the combined application of the PAT techniques for reconstructing the reconstructed data and the adaptation of the signal model in a single step.

This effect can be expressed in the form of the noise propagation. As explained above, it is assumed that the MR data has been decorrelated and noise levels in each channel have been normalized. This means that the noise covariance matrix can be notated as:

$$\langle y_{\{l,i\}} y_{\{J,j\}}^\dagger \rangle = \sigma^2 \delta_{I,J} \delta_{i,j}. \quad (20)$$

Furthermore, phase maps typically are comparatively constant and therefore their contribution to the noise in the reconstructed water images and fat images can be substantially reduced. For this reason, the contribution of the phase maps to the noise can be discounted in a first approach. The following is obtained:

$$\Delta y_{\{l,e\}} = \sum_{x,m} A_{\{l,e\},x} \phi_e(x) c_{e,m} \Delta V_m(x) \quad (21)$$

$$\equiv \sum_{x,m} B_{\{l,e\},\{x,m\}} \Delta V_m(x).$$

The noise correlation in the determined parameters is then given by $$\langle V_m(x) V_n(y)^\dagger \rangle = \sigma^2 (B^\dagger B)_{\{m,x\},\{n,y\}}^{-1}. \quad (22)$$

An example of the effect of the proposed techniques can be given for the simplified case in which the phase can be ignored, i.e. $\varphi_e(x) = 1$, and be chosen in the echo times according to minimum noise propagation for the Dixon technique. In this case the following is obtained:

$$B_{\{l,i\},\{x,m\}} \approx A_{\{l,i\},x}. \quad (23)$$

A g-factor is obtained which is equivalent to the noise amplification that corresponds to the overlaid undersampling schemes. For a comparatively large number of echoes or MR contrasts, a noise amplification of the PAT techniques can therefore be greatly reduced—up to the point at which no noise amplification at all or no significant noise amplification results from the PAT technique, but only from the reduced measurement duration.

Phase unwrapping and variable projection techniques can be utilized in order to determine the phase maps. For example, for each pixel of the result image, determining the result image can additionally include: Performing a phase unwrapping operation for phase correction of the respective pixel. The phase unwrapping can take into account results of the non-linear optimization of a plurality of pixels of the result image which are adjacent to the respective pixel.

Generally, different approaches can be taken into account: Firstly, it would be e.g. possible to use a non-linear optimizer in order to calculate different minima of $\tilde{X}_2$. The minimum having the lowest value of $\tilde{X}_2$ an be used as the end result. This approach is particularly suitable if a greater number of signal echoes or MR contrasts is present or if a good spectral signal model is predefined for the fat component. Secondly, it may also be possible to calculate different minima of $\tilde{X}_2$ means of a non-linear optimizer. These different minima can be used as candidates for each pixel/voxel. The correct minimum can be determined by means of a conventional phase unwrapping function. Thirdly, it may be possible to use a global optimization strategy in order to ensure a constant phase map, and moreover in particular without calculating minima at each pixel/voxel in a preceding step. This can be achieved by means of an optimization function which ensures a constant phase map and a low value of $\tilde{X}_2$. In a simple case this is the sum of a squared gradient of the phase map and all of the $\tilde{X}_2$ values. In all of the above-cited cases, a variable projection technique can be used in order to eliminate the water and fat components analytically from the optimization strategy and to perform the remaining optimization numerically. Such techniques in conjunction with chemical-shift MR imaging are also known to the person skilled in the art from the German patent applications DE 10 2013 217 651.1 and DE 10 2013 217 650.3.

To sum up, it has therefore been explained in the foregoing with the aid of general techniques and concrete examples how it is possible, through the use of different undersampling schemes for the various MR contrasts, to achieve a lower level of noise in the MR contrasts or, as the case may be, in the result image.

Such techniques as described hereinabove can be implemented e.g. by means of an MR system 100, as shown in FIG. 1. The MR system 100 has a magnet 110 which defines a tube 111. The magnet 110 is able to generate a basic magnetic field parallel to its longitudinal axis. The basic magnetic field may exhibit inhomogeneities, i.e. local deviations from a reference value. An object undergoing examination, in this case an examination subject 101, can be introduced into the magnet 110 on a support table 102. The MR system 100 additionally has a gradient system 140 for generating gradient fields that are used for MR imaging and for spatial encoding of acquired raw data. Typically, the gradient system 140 comprises at least three separately drivable gradient coils 141 which are positioned in a well-defined arrangement relative to one another. The gradient coils 141 enable gradient fields to be applied and switched along specific spatial directions (gradient axes). As a result of the switching of the gradient fields, eddy current effects can be provoked which produce local magnetic fields. The gradient fields can be used e.g. for slice selection, for frequency encoding (in the readout direction) and for phase encoding. A spatial encoding of the raw data can be achieved in that way. The spatial directions, which stand parallel to slice selection gradient fields, phase encoding gradient fields and readout gradient fields respectively, do not necessarily have to be coincident with the machine coordinate system. Rather, they can be defined e.g. in relation to a k-space trajectory, which in turn can be specified on the basis of specific requirements of the respective MR measurement sequence and/or can be specified on the basis of anatomical features of the examination subject 101.

In order to excite the polarization or alignment of the nuclear spins resulting in the basic magnetic field or the magnetization in the longitudinal direction, an RF coil array 121 is provided which can radiate an amplitude-modulated RF excitation pulse into the examination subject 101. A transverse magnetization can be generated by this means. In order to generate such RF excitation pulses, an RF transmitter unit 131 is connected to the RF coil array 121 via an RF switch 130. The RF transmitter unit 131 can comprise an RF generator and an RF amplitude modulation unit. The RF excitation pulses can tilt the transverse magnetization 1 d slice-selectively or 2D/3D spatially selectively or globally from the rest position.

In addition, an RF receiver unit 132 is coupled to the RF coil array 121 via the RF switch 130. MR signals of the relaxing transverse magnetization can be acquired as MR data via the RF receiver unit 132, e.g. by inductive coupling into the RF coil array 121. The MR data can map an examination region 190. The MR data can correspond to the raw data; it is, however, also possible for the raw data to be processed further in order to obtain the MR data. For example, the raw data present in the k-space can be Fourier-transformed in order thereby to obtain MR data in the image space.

Generally, it is possible to use separate RF coil arrays 121 for the application of the RF excitation pulses by means of the RF transmitter unit 131 and for the acquisition of the MR data by means of the RF receiver unit 132. For example, a volume coil 121 can be used for applying RF pulses, and a surface coil (not shown) consisting of an array of RF coils for the acquisition of raw data. The surface coil for acquiring the raw data may, for example, consist of thirty-two individual RF coils and consequently be particularly suitable for PAT techniques. Analogous techniques are known to the person skilled in the art, so no further details need to be explained here.

The MR system 100 additionally has an operator control unit 150, which may comprise e.g. a screen, a keyboard, a mouse, etc. User input can be acquired and output to the user realized by means of the operator control unit 150. For example, it can be possible for individual operating modes or operating parameters of the MR system 100 to be set by the user and/or automatically and/or by remote control by means of the operator control unit 150.

In addition, the MR system 100 has a computing unit 160. The computing unit 160 can be configured e.g. to perform various computing operations within the framework of determining a result image based on chemical-shift MR imaging and/or parametric MR imaging.

Figure 2:
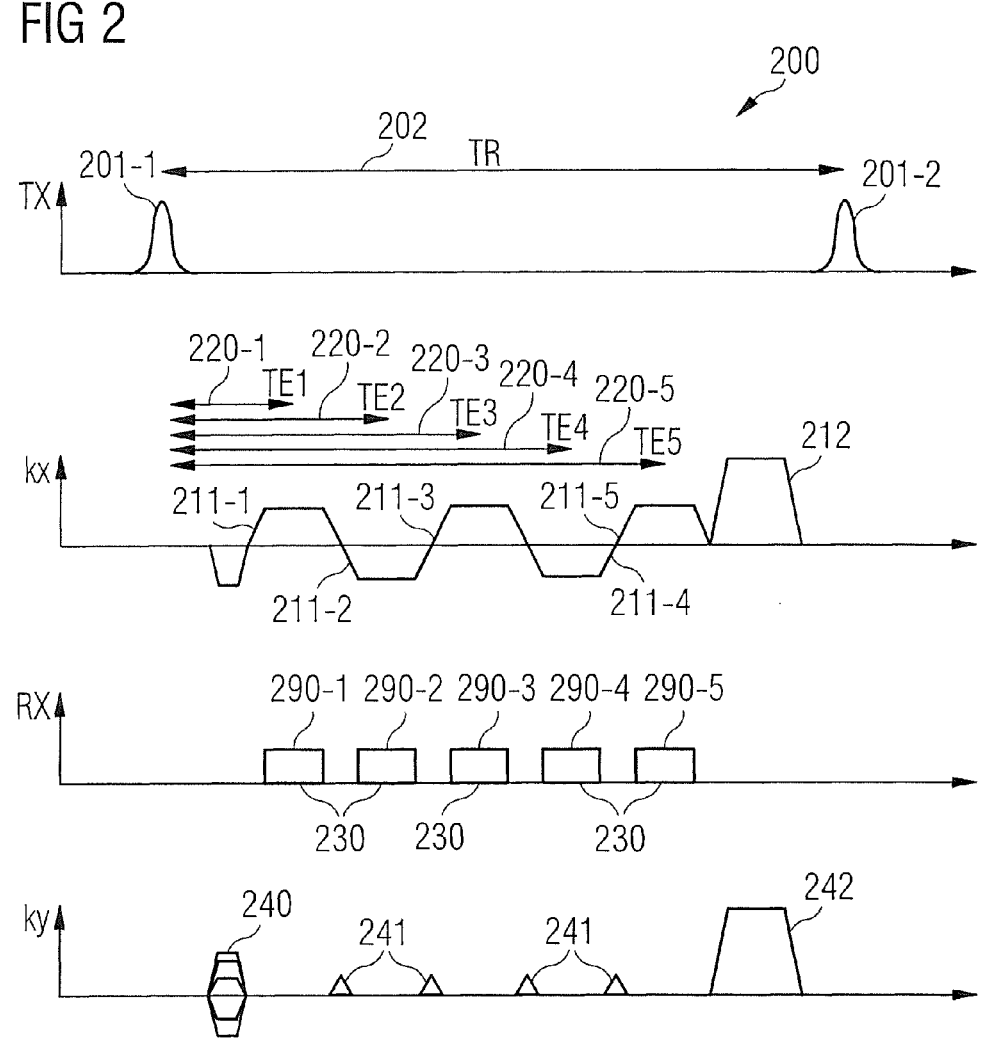
FIG. 2 shows a measurement sequence which acquires MR data for different MR contrasts, wherein chemical-shift MR imaging can be performed based on the MR contrasts.

FIG. 2 shows a gradient echo (GRE) measurement sequence 200 which acquires MR data that can be used for chemical-shift MR imaging, in particular for fat/water separation in accordance with Dixon techniques. Firstly, an RF excitation pulse 201-1 is applied (shown right at the top in FIG. 2 in the transmit line TX). The RF excitation pulse 201-1 prepares the magnetization in the examination region 190, i.e. it can be e.g. a 2D slice-selective RF excitation pulse 201-1 which excites the nuclear spins in a slice arranged orthogonally to the slice selection direction kz. To that end, a gradient pulse can be switched along the slice selection direction kz (not shown in FIG. 2). It would also be possible, within the context of 3D MR imaging for example, to apply a 3D slice-selective MR excitation pulse 201-1 in order to prepare the magnetization in the examination region 190.

A phase-encoding gradient pulse 240 is switched in the phase encoding direction ky. Said pulse selects e.g. a specific k-space line. A gradient echo train consisting of a number of bipolar gradient pulses 211-1-211-5 is then switched in the readout direction kx (shown in the second line from the top in FIG. 2). The gradient pulses 211-1-211-5 form gradient echoes at specific echo times or time points 220-1-220-5 relatively in relation to the preparation of the magnetization by means of the RF excitation pulse 201-1. For the different gradient echoes, MR data can be acquired along a k-space line which is oriented orthogonally to the phase encoding direction ky and parallel to the readout direction kx by defining readout time intervals 230 (shown in the third line from the top, receive line RX, in FIG. 2). Said MR data at the different time points 220-1-220-5 is associated with different MR contrasts 290-1-290-1. The MR data for the plurality of MR contrasts 290-1-290-5 is therefore acquired at different time points 220-1-220-5 in each case following the preparation of the magnetization by application of the RF excitation pulse 201-1.

FIG. 2 illustrates a situation in which not all of the MR data can be acquired for the different MR contrasts 290-1-290-5 following the one-time preparation of the magnetization by application of the RF excitation pulse 201-1. For this reason, a further RF excitation pulse 201-2 (shown on the right in the TX line in FIG. 2) is applied after a defined repetition time TR, 202. Further MR data can then be acquired for the different MR contrasts 290-1-290-5, e.g. by variation of the phase encoding gradient pulse 240 (not shown in FIG. 2). The MR data of a specific MR contrast 290-1-290-5 is then composed of the MR data acquired for the different repetitions of the measurement sequence 200.

The various MR data is acquired in the readout time intervals 230 for specific k-space points. Said k-space points are arranged in the k-space according to an undersampling scheme. For example, the k-space can be undersampled along the phase encoding direction ky, i.e. individual k-space lines can be omitted. This can be achieved through suitable choice of the phase encoding gradient pulse 240 for the different repetitions. For example, the phase encoding gradient pulse 240 could be varied in each case in such a way that MR data is acquired only every second or third or fourth k-space line; this corresponds to an acceleration factor of the respective undersampling scheme.

In the scenario shown in FIG. 2, the undersampling schemes of the different MR contrasts 290-1-290-5 are different. This is achieved by switching short gradient pulses 241 along the phase encoding direction ky between the readout time intervals 230 of MR contrasts 290-1-290-5 adjacent in time. Because the gradient pulses 241 are embodied as short spikes (called "blips"), the undersampling schemes of the different MR contrasts 290-1-290-5 are shifted relative to one another along the phase encoding direction ky, e.g. by one k-space point at a time. The other parameters of the undersampling schemes, such as e.g. in particular the acceleration factor, do not change. It would, however, also be possible, e.g. by means of a different temporal arrangement of the repetitions, etc. and switching of further phase encoding gradient pulses 240, to implement other types of undersampling schemes for the different MR contrasts 290-1-290-5. Thus, FIG. 2 depicts a scenario in which the undersampling schemes for the different MR contrasts 290-1-290-5 are shifted relative to one another by switching of the gradient pulses 241. Generally, the most diverse techniques are possible in order to ensure that the undersampling schemes for the different MR contrasts 290-1-290-5 are different from one another.

In the foregoing, a GRE measurement sequence 200 which can be used in connection with chemical-shift MR imaging was discussed in relation to FIG. 2. It is, however, possible to employ analogous techniques also for measurement sequences 200 which can be used for parametric MR imaging. For example, a Look-Locker-type measurement sequence 200 could be used for parametric MR imaging. Instead of one or more RF excitation pulses 201-1, 201-2, one or more RF inversion pulses can then be applied (not shown in FIG. 2). Instead of the water fraction and the fat fraction, the magnetic parameter can then be selected from the following group: T1 relaxation time; T2 relaxation time; saturation magnetization; and flip angle.

Figure 3:
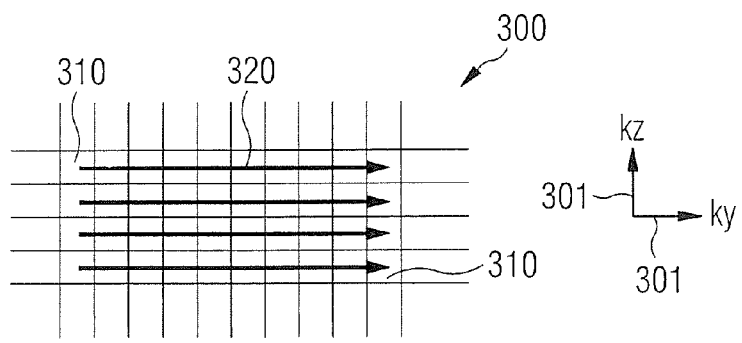
FIG. 3 shows a Cartesian k-space trajectory.

In the main, details relating to the different undersampling schemes are explained hereinbelow. A schematic illustration of k-space 300 is shown in FIG. 3. The phase encoding direction ky is the horizontal k-space direction 301 in FIG. 3. The slice selection direction kz is the vertical k-space direction 301 in FIG. 3. FIG. 3 depicts a Cartesian k-space trajectory 320 which sequentially samples different k-space points 310—in FIG. 3, a k-space point 310 denotes a k-space line along the readout direction kx (not shown in FIG. 3). In this case the k-space points lie on a square grid in k-space 300.

Figure 4:
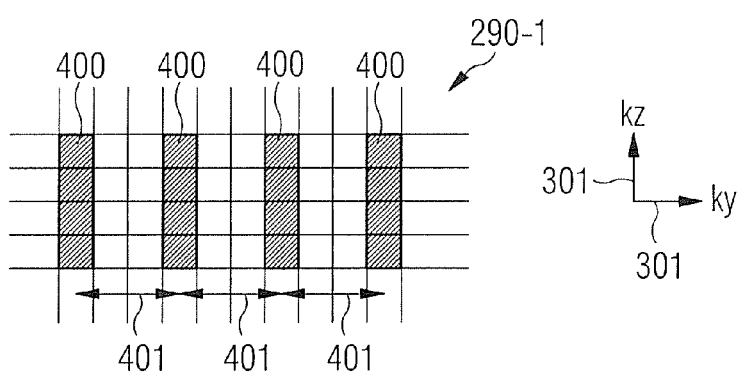
FIG. 4 shows an undersampling scheme for a first MR contrast for the k-space trajectory of FIG. 3, wherein an image acceleration is performed along a phase encoding direction.

In FIG. 4, MR data is acquired for a first MR contrast 290-1. FIG. 4 shows an undersampling scheme 400 for the acquisition of MR data for the k-space points 310 along the k-space trajectory 320. In this case black (white) illustrates that MR data (no MR data) is acquired for the respective k-space point 310. It can be seen from FIG. 4 that adjacent k-space points 310 for which MR data is acquired are spaced at an equal and constant distance 401 along the phase encoding direction ky. Along the phase encoding direction ky, MR data is acquired for every third k-space point 310 along the k-space trajectory 320, i.e. the acceleration factor for the phase encoding direction ky equals three. No image acceleration or undersampling of k-space 300 is present along the slice selection direction kz and the readout direction kx (not shown in FIG. 4).

Figure 5:
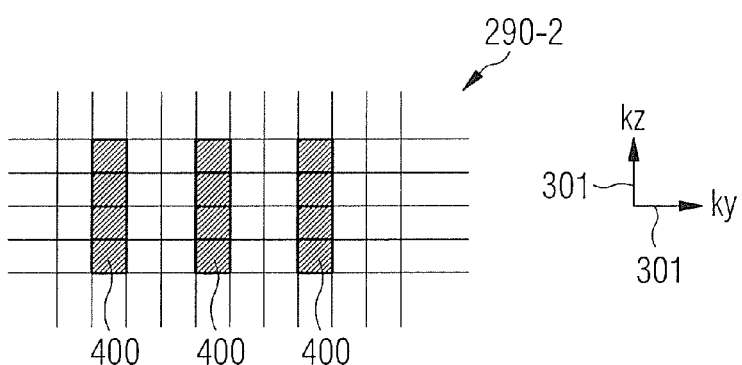
FIG. 5 shows an undersampling scheme for a second MR contrast which is shifted relative to the undersampling scheme according to FIG. 4 for the first MR contrast.

FIG. 5 illustrates a scenario in which MR data is acquired for a second MR contrast 290-2. In the scenario shown in FIG. 5, the MR data is acquired for k-space points 310 along the k-space trajectory 320 according to an undersampling scheme 400 which is different from the undersampling scheme 400 of FIG. 4. In particular, the undersampling scheme 400 of the second MR contrast 290-2 (see FIG. 5) is shifted by one k-space point 310 along the k-space trajectory 320 in the phase encoding direction ky, for which the acceleration factor equals three. The same applies analogously to the undersampling scheme 400, which is used for acquiring MR data for the third MR contrast 290-3 (see FIG. 6).

Figure 6:
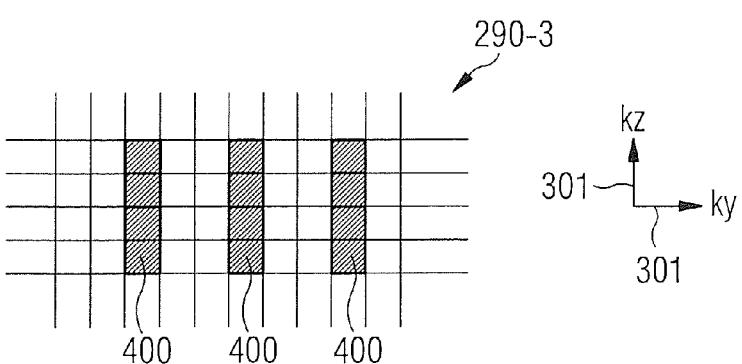
FIG. 6 shows an undersampling scheme for a third MR contrast which is shifted relative to the undersampling scheme for the first and second MR contrasts according to FIGS. 4 and 5.

It is apparent from a comparison of FIGS. 4-6 that the different undersampling schemes 400 of the MR contrasts 290-1-290-3 are shifted relative to one another in such a way that MR data for an MR contrast 290-1-290-5 is acquired for each k-space point 310 along the k-space trajectory 320. In other words, an overlaying of the undersampling schemes 400 of the different MR contrasts 290-1-290-5 leaves no gaps in the k-space 300; the acceleration factor with the overlaying of the undersampling schemes 400 equals one. This can result in the noise component due to the PAT technique being comparatively small.

Techniques of 2D MR imaging have been explained in the foregoing. Similar techniques can also be applied to 3D MR imaging (cf. FIGS. 7-10). In that case the slice selection direction kz can be used as a further phase encoding direction. A situation is shown in FIGS. 7-10 in which the undersampling scheme has an acceleration factor of two in both k-space directions 301 kz, ky that are used for phase encoding. The acceleration factor in the readout direction kx in turn equals one (not shown in FIGS. 7-10). Also, the undersampling schemes 400 are shifted relative to one another in such a way that an overlaying of the undersampling schemes 400 is equivalent to a full sampling of the k-space 300, i.e. has no, or no significant, acceleration factor.

Figure 11:
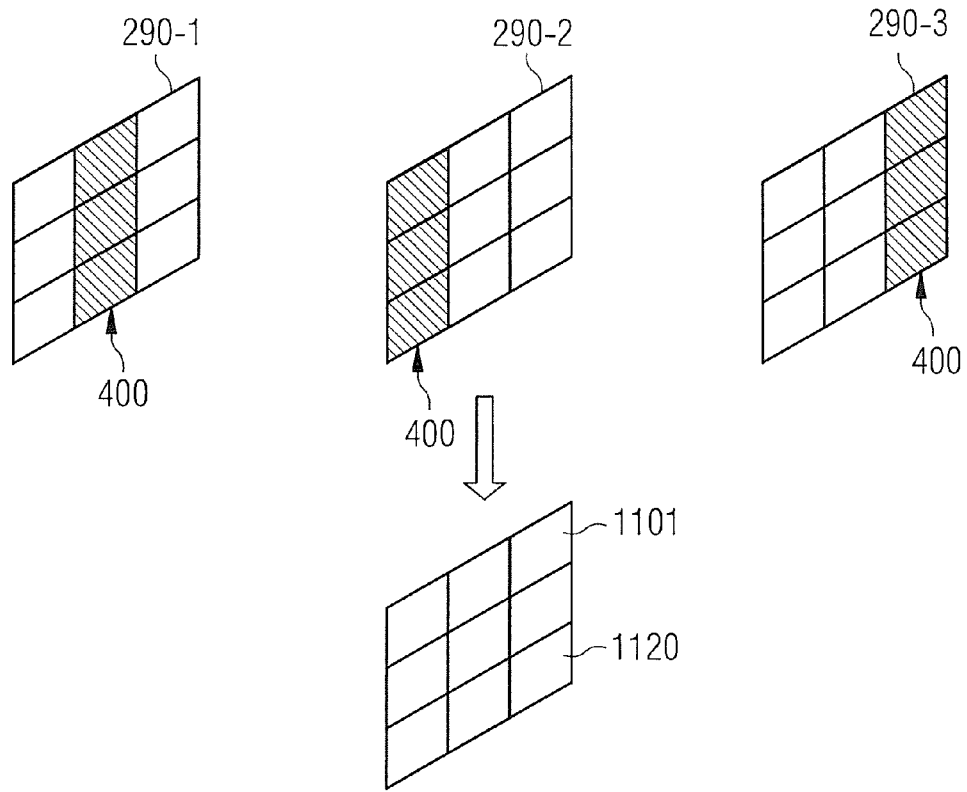
FIG. 11 schematically shows the MR contrasts and a result image which is indicative of a magnetic parameter.

FIG. 11 shows the different MR contrasts 290-1-290-3. It is shown once again, purely illustratively, that the different undersampling schemes 400 are shifted relative to one another. The result image 1101 can then be determined. In a simple implementation, MR data can be reconstructed based on the PAT techniques in the k-space 300 and/or in the image space for each MR contrast 290-1-290-3. For each pixel 1120 of the result image 1101, the magnetic parameter can then be determined as a pixel value by adapting the respective signal model to the MR data of the different MR contrasts 290-1-290-5.

It would, however, also be possible for the reconstruction of the reconstructed data for each pixel 1120 of the result image 1101 to take place in an interconnected optimization step together with the determination of the magnetic parameter by adaptation of the signal model.

Figure 12:
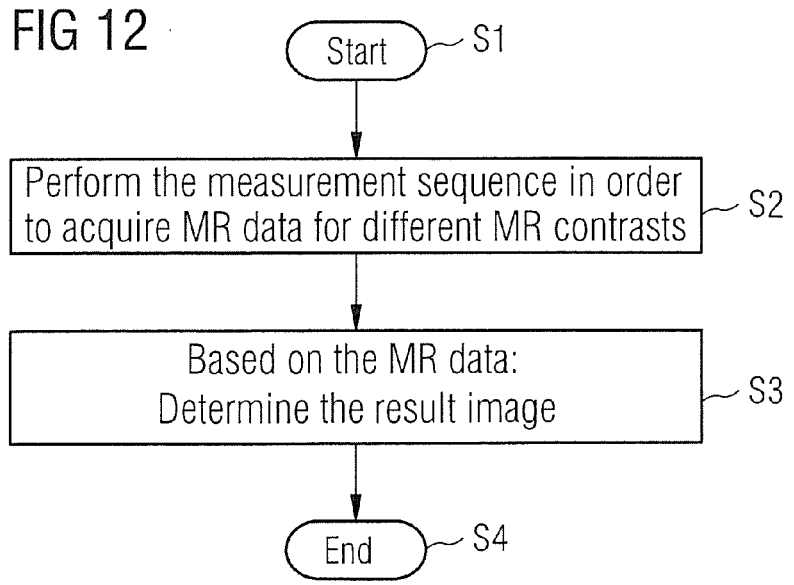
FIG. 12 is a flowchart of a method for MR imaging according to different embodiment variants.

FIG. 12 shows a flowchart of a method for MR imaging according to different embodiment variants. The method starts at step S1. First, in step S2, the measurement sequence 200 is performed in order to acquire the MR data for the different MR contrasts 290-1-290-5. For example, a GRE measurement sequence 200 or a Look-Locker measurement sequence could be performed in step S2. A spin-echo measurement sequence 200 could also be performed within the context of chemical-shift MR imaging.

The post-processing of the acquired MR data then takes place in step S3. In particular, the result image 1101 is determined in step S3 on the basis of the acquired MR data. In step S3, reconstructed data is reconstructed by means of PAT techniques and in addition the MR parameter is determined by adapting a signal model to the acquired MR data and/or to the reconstructed MR data. The method ends at step S4.

Figure 13:
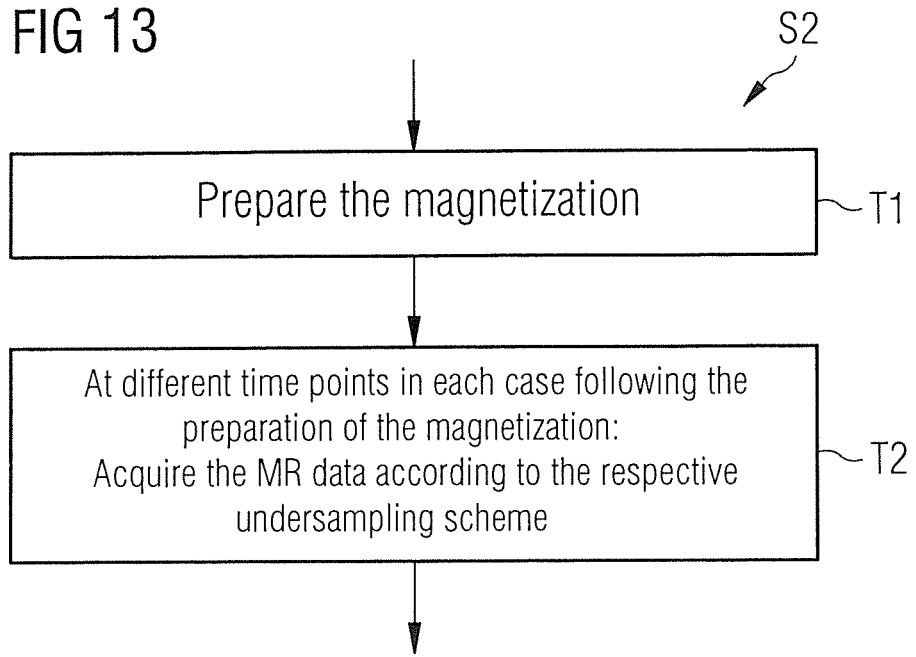
FIG. 13 is a flowchart representing method steps of the method of FIG. 12 in connection with the performance of the measurement sequence with greater detail.

Step S2 is illustrated in more detail in FIG. 13. First, the preparation of the magnetization is carried out in step T1. For example, an RF inversion pulse or an RF excitation pulse 201-1, 201-2 can be applied in step T1. It is also possible to apply a plurality of RF pulses.

Next, in step T2, the MR data is acquired according to a respective undersampling scheme 400. In step T2, the MR data for the different MR contrasts 290-1-290-5 is acquired at different time points 220-1-220-5 in each case in relation to the preparation in step T1. The undersampling schemes 400 used in step T2 for the different MR contrasts 290-1-290-5 are different from one another (cf. Eq. 3). Preferably, an overlaying of the undersampling schemes has no, or only a slight, acceleration.

Figure 14:
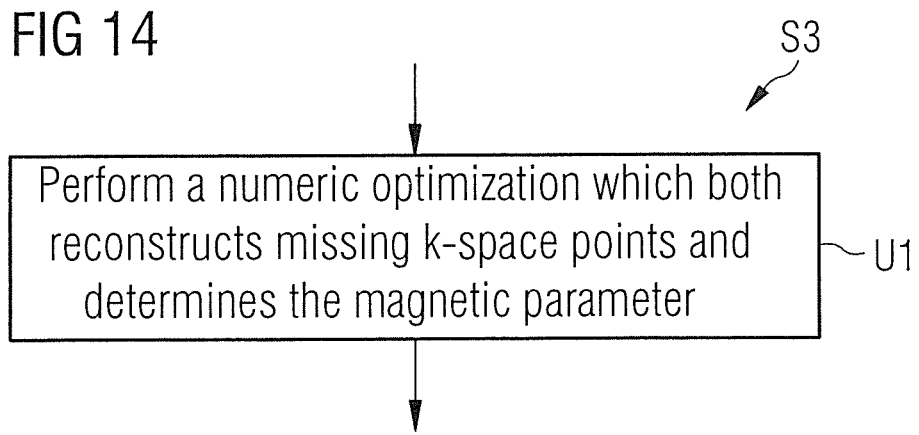
FIG. 14 is a flowchart representing method steps of the method of FIG. 12 in connection with the determination of the result image with greater detail.

FIG. 14 illustrates step S3 (see FIG. 12) in more detail. In the scenario shown in FIG. 14, a single interconnected numeric optimization is performed in step U1. In the course of the numeric optimization, both a reconstruction based on PAT techniques is performed and the signal model is adapted to the acquired MR data and the reconstructed data in order thereby to determine the magnetic parameter (cf. Eq. 6 and 7 and Eq. 15 and 18, respectively).

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for magnetic resonance (MR) imaging, comprising:
    operating an MR scanner, while an examination subject is situated therein, to execute an MR data acquisition sequence wherein MR data are acquired from an examination region of the examination subject with a plurality of different MR contrasts at respectively different points in time, and entering the MR data for each MR contrast at k-space points in an electronic memory, representing k-space;
    in said MR data acquisition sequence, operating the MR scanner to prepare nuclear spins in the examination region prior to each acquisition of MR data for each of said MR contrasts;
    in said MR data acquisition sequence, operating the MR scanner to enter the MR data for each MR contrast at respective k-space points so that k-space is undersampled according to a respective undersampling scheme, with each undersampling scheme for each of said MR contrasts being different;
    from a computer, accessing said MR data from said electronic memory and calculating a result image from the MR data, said result image being comprised of pixels having respective pixel values that indicate a value of a magnetic parameter in said examination region; and
    making said result image available in electronic format an output of the computer as a data file.

2. A method as claimed in claim 1 wherein each of said different undersampling schemes has a same acceleration factor along same directions in k-space.

3. A method as claimed in claim 2 wherein said acceleration factor is greater than 4.

4. A method as claimed in claim 2 wherein said acceleration factor is greater than 7.

5. A method as claimed in claim 1 wherein the respective, different undersampling schemes of the magnetic resonance contrasts are shifted with respect to each other to cause MR data acquired for at least one MR contrast to be shifted by a k-space point along a k-space trajectory.

6. A method as claimed in claim 1 wherein said k-space points are arranged along a k-space trajectory, and wherein the respective undersampling schemes for acquisitions of different MR contrasts that are acquired at adjacent points in time are shifted by one k-space point along said k-space trajectory in a k-space direction for which an acceleration factor is greater than one.

7. A method as claimed in claim 1 wherein said k-space points are arranged along a Cartesian k-space trajectory in k-space, and within a distance along said Cartesian k-space trajectory between k-space points for which said MR data are acquired according to a respective undersampling scheme is constant and corresponds to an acceleration factor for the respective undersampling scheme.

8. A method as claimed in claim 1 comprising reconstructing each pixel of said result image using a parallel imaging technique.

9. A method as claimed in claim 1 comprising calculating each pixel of the result image using an interconnected optimization.

10. A method as claimed in claim 1 comprising calculating said result image by, for each pixel, determining said magnetic parameter as a pixel value by adapting a signal model to at least one of respective MR data of the different MR contrasts or to reconstructed data obtained with a parallel imaging technique.

11. A method as claimed in claim 10 comprising calculating each pixel of the result image using an interconnected optimization.

12. A method as claimed in claim 1 comprising preparing said nuclear spins by operating said MR scanner in said MR data acquisition sequence to radiate a radio-frequency inversion pulse, and selecting said magnetic parameter from the group consisting of T1 relaxation time, T2 relaxation time, saturation magnetization, and flip angle.

13. A method as claimed in claim 1 comprising preparing said magnetization of nuclear spins by operating said MR scanner in said MR data acquisition sequence to radiate a radio-frequency excitation pulse, and wherein said magnetic parameter is a fraction of a spin species in said examination region.

14. A method as claimed in claim 13 comprising selecting said spin species from the group consisting of fat and water.

15. A method as claimed in claim 13 comprising determining said magnetic parameter for a plurality of pixels in said result image by performing a phase unwrapping for phase correction of the respective pixel, with said phase unwrapping accounting for a non-linear optimization of said plurality of pixels in said result image that are adjacent to the respective pixel.

16. A magnetic resonance (MR) apparatus comprising:
    an MR scanner;
    an electronic memory;
    a control computer configured to operate the MR scanner, while an examination subject is situated therein, to execute an MR data acquisition sequence wherein MR data are acquired from an examination region of the examination subject with a plurality of different MR contrasts at respectively different points in time, and entering the MR data for each MR contrast at k-space points in said electronic memory, representing k-space;
    said control computer being configured to operate the MR scanner in said MR data acquisition sequence to prepare nuclear spins in the examination region prior to each acquisition of MR data for each of said MR contrasts;
    said control computer being configured to operate the MR scanner in said MR data acquisition sequence to enter the MR data for each MR contrast at respective k-space points so that k-space is undersampled according to a respective undersampling scheme, with each undersampling scheme for each of said MR contrasts being different;
    a computer configured to access said MR data from said electronic memory and to calculate a result image from the MR data, said result image being comprised of pixels having respective pixel values that indicate a value of a magnetic parameter in said examination region; and
    said computer being configured to make said result image available in electronic format an output of the computer as a data file.

17. A magnetic resonance (MR) apparatus comprising:

an MR scanner;

an electronic memory;

a control computer configured to operate the MR scanner, while an examination subject is situated therein, to execute an MR data acquisition sequence wherein MR data are acquired from an examination region of the examination subject with a plurality of different MR contrasts at respectively different points in time, and entering the MR data for each MR contrast at k-space points in said electronic memory representing k-space;

said control computer being configured to operate the MR scanner in said MR data acquisition sequence to prepare nuclear spins in the examination region prior to each acquisition of MR data for each of said MR contrasts;

said control computer being configured to operate the MR scanner in said MR data acquisition sequence to enter the MR data for each MR contrast at respective k-space points so that k-space is undersampled according to a respective undersampling scheme, with each undersampling scheme for each of said MR contrasts being different;

a computer configured to access said MR data from said electronic memory and to calculate a result image from the MR data using a parallel imaging technique for each pixel of the result image, said result image then being comprised of pixels having respective pixel values that indicate a value of a magnetic parameter in said examination region;

said computer being configured to calculate each pixel of the result image using an interconnected optimization and by, for each pixel, determining said magnetic parameter as a pixel value by adapting a signal model to at least one of respective MR data of the different MR contrasts or to reconstructed data obtained with a parallel imaging technique; and said computer being configured to make said result image available in electronic format an output of the computer as a data file.

* * * * *